(12) United States Patent
Ando (10) Patent No.: US 9,668,642 B2
(45) Date of Patent: Jun. 6, 2017

(54) MEDICAL INSTRUMENT AND BENDING DEFORMATION DEVICE

(71) Applicant: CANON KABUSHIKI KAISHA, Tokyo (JP)

(72) Inventor: Masahiro Ando, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 51 days.

(21) Appl. No.: 14/404,399

(22) PCT Filed: May 17, 2013

(86) PCT No.: PCT/JP2013/003155
§ 371 (c)(1),
(2) Date: Nov. 26, 2014

(87) PCT Pub. No.: WO2013/179601
PCT Pub. Date: Dec. 5, 2013

(65) Prior Publication Data
US 2015/0112142 A1   Apr. 23, 2015

(30) Foreign Application Priority Data
May 31, 2012   (JP) .................................. 2012-124502

(51) Int. Cl.
*A61B 1/00* (2006.01)
*A61B 1/005* (2006.01)
*G02B 23/24* (2006.01)
*A61B 1/04* (2006.01)

(52) U.S. Cl.
CPC .......... *A61B 1/0057* (2013.01); *A61B 1/0052* (2013.01); *A61B 1/00105* (2013.01); *A61B 1/00128* (2013.01); *G02B 23/2476* (2013.01)

(58) Field of Classification Search
CPC . A61B 1/0052; A61B 1/0057; A61B 1/00128; A61B 1/00105
USPC .................................. 600/139, 141, 146, 147
See application file for complete search history.

(56) References Cited

U.S. PATENT DOCUMENTS

| | | | |
|---|---|---|---|
| 7,722,532 B2* | 5/2010 | Ikeda | A61B 1/00039 600/102 |
| 8,070,685 B2 | 12/2011 | Harhen et al. | |
| 2006/0287576 A1* | 12/2006 | Tsuji | A61B 1/00105 600/132 |
| 2007/0232856 A1 | 10/2007 | Ueno et al. | |
| 2009/0149702 A1* | 6/2009 | Onoda | A61B 1/00112 600/102 |

(Continued)

FOREIGN PATENT DOCUMENTS

| | | |
|---|---|---|
| JP | 2-161928 A | 6/1990 |
| JP | 5-20704 U | 3/1993 |
| JP | 2000-14628 A | 1/2000 |

(Continued)

*Primary Examiner* — Timothy J Neal
(74) *Attorney, Agent, or Firm* — Canon U.S.A., Inc. IP Division (57) ABSTRACT

The present invention provides a decoupling and coupling type medical instrument which includes a bending deformation portion and a manipulation unit. The medical instrument is excellent in operability while preventing removal, cutting and the like of a wire of the bending deformation portion. A medical instrument which satisfies $0<T1<T2$ in which tension in a wire is $T1$ in a decoupled state and is $T2$ in a coupled state.

17 Claims, 6 Drawing Sheets

(56) References Cited

U.S. PATENT DOCUMENTS

2012/0100729 A1* 4/2012 Edidin .............. H01R 13/6205
439/38

FOREIGN PATENT DOCUMENTS

| JP | 2003-127085 A | 5/2003 |
|----|---------------|--------|
| JP | 2005279253 A | 10/2005 |
| JP | 2009-160243 A | 7/2009 |
| JP | 2009-225876 A | 10/2009 |
| JP | 2010-194102 A | 9/2010 |
| WO | 2006/059721 A1 | 6/2006 |
| WO | 2007/007873 A1 | 1/2007 |
| WO | 2009/035051 A | 3/2009 |

* cited by examiner

MEDICAL INSTRUMENT AND BENDING DEFORMATION DEVICE

TECHNICAL FIELD

The present invention relates to a medical instrument in which a bending deformation portion and a manipulation unit may be coupled to and decoupled from each other. The present invention relates also to a bending deformation device which is the bending deformation portion.

BACKGROUND ART

In a decoupling type endoscope described in PTL1, an inserting portion and a manipulation unit are decoupled from each other. The inserting portion includes a wire for transmitting force to a bending portion of the inserting portion. Slack of the wire may be easily removed by an operator manipulating the manipulation unit when the manipulation unit is coupled to the inserting portion.

CITATION LIST

Patent Literature

PTL 1: Japanese Patent Laid-Open No. 2010-194102

SUMMARY OF INVENTION

Increasing tension in a wire in a state in which the manipulation unit is coupled to the inserting portion for manipulation is described in PTL1. However, no tension is applied (tension is 0) to the inserting portion of the decoupled state.

Therefore, the wire of the inserting portion of the decoupled state may be slacked and it is necessary to prevent the damage to the wire during, for example, conveyance.

SOLUTION TO PROBLEM

The present invention provides a medical instrument, including: an elongated bending deformation portion which includes a wire therein and which is bent by at least one of pulling and pushing the wire; and a manipulation unit which transmits power to the wire, wherein: the medical instrument includes a coupling and decoupling unit which decouples or couples the bending deformation portion and the manipulation unit; the bending deformation portion includes a tension applying unit which applies tension to the wire; and a relationship between tension T1 in the wire applied by the tension applying unit when the bending deformation portion and the manipulation unit are decoupled and tension T2 in the wire applied by the tension applying unit when the bending deformation portion and the manipulation unit are coupled satisfies $0<T1<T2$.

The present invention also provides a bending deformation device of a medical instrument, including: an elongated bending deformation device which includes a wire therein and which is bent by at least one of pulling and pushing the wire; and a manipulation device which transmits power to the wire, wherein: the bending deformation device includes at least a part of a coupling and decoupling unit which decouples or couples the bending deformation device and the manipulation device; the bending deformation device includes a tension applying unit which applies tension to the wire; and a relationship between tension T1 in the wire applied by the tension applying unit when the bending deformation device and the manipulation device are decoupled and tension T2 in the wire applied by the tension applying unit when the bending deformation device and the manipulation device are coupled satisfies $0<T1<T2$.

Further features of the present invention will become apparent from the following description of exemplary embodiments with reference to the attached drawings.

DESCRIPTION OF EMBODIMENTS

First Embodiment

A medical instrument according to a first embodiment of the present invention includes a bending deformation portion and a manipulation unit which may be coupled to and decoupled from each other. The bending deformation portion includes therein a wire for bending deformation. When tension in the wire of a decoupled state is represented by T1 and tension in the wire of a coupled state is represented by T2, the following relationship is satisfied: $0<T1<T2$.

Figure 1:
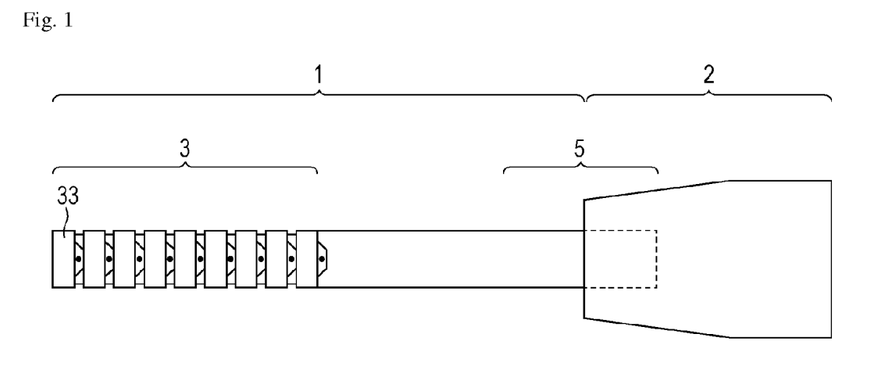
FIG. 1 is a schematic diagram illustrating a medical instrument according to a first embodiment.

First, reference signs in the drawings will be described. Reference sign 1 denotes a bending deformation portion, 2 denotes a manipulation unit, 6 and 7 denote wires, 23 and 24 denote stoppers, 8 denotes a rotating member, 19 denotes a spring, 9, 10, 11 and 12 denote magnets, 13 and 14 denote wires, and 15, 16, 17 and 18 denote magnets. FIG. 1 is a schematic diagram illustrating the medical instrument according to the first embodiment.

The medical instrument according to the present embodiment includes a bending deformation portion 1 and a manipulation unit 2. The bending deformation portion 1 and the manipulation unit 2 may be coupled to and decoupled from each other by an unillustrated coupling and decoupling unit. The coupling and decoupling unit will be described later with reference to FIG. 2.

As illustrated in FIG. 1, the bending deformation portion 1 has an elongated shape with a left end of the drawing being a tip 3 and a right end of the drawing being a base 5. FIG. 1 illustrates a state in which the bending deformation portion 1 and the manipulation unit 2 are coupled to each other. A part of the base 5 is disposed inside the manipulation unit 2.

The bending deformation portion 1 includes therein a wire (not illustrated) extending in the direction of the tip 3 and the base 5. The tip 3 makes bending deformation when the wire is pulled and pushed.

The tip 3 includes a plurality of frames 33 and makes bending deformation among the frames.

Figure 2:
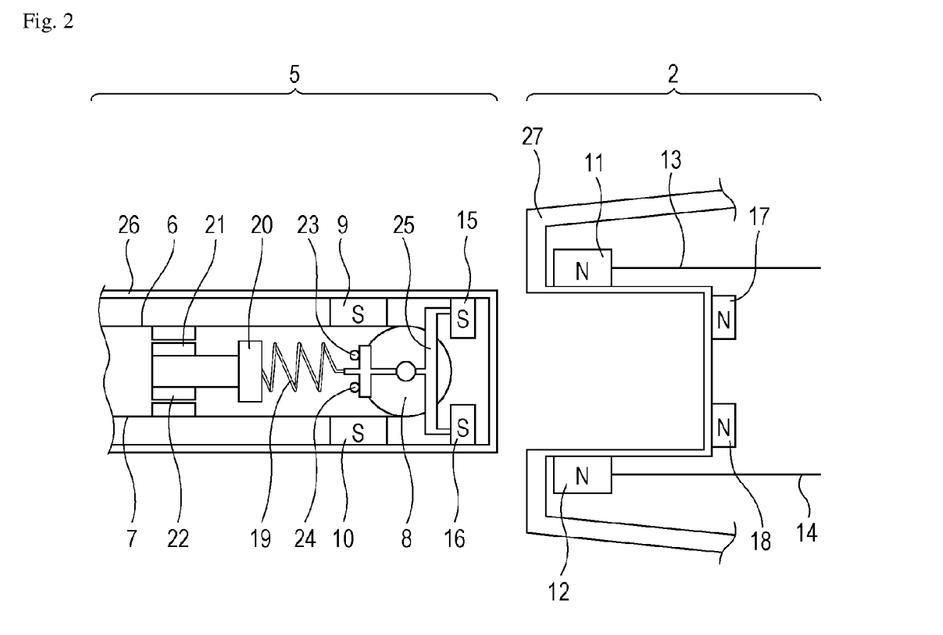
FIG. 2 is a schematic sectional view illustrating a state in which the medical instrument according to the first embodiment has been decoupled.

FIG. 2 is a schematic sectional view illustrating the base 5 of the bending deformation portion 1 and the manipulation unit 2. FIG. 2 illustrates a state in which the bending deformation portion 1 and the manipulation unit 2 are decoupled from each other.

The bending deformation portion 1 includes wires 6 and 7 disposed inside a housing 26. The wires 6 and 7 are supported by a rotating member (for example, a pulley) 8 which is a support member and is pulled (i.e., pulled in the direction from the left to the right in FIG. 2) and pushed (i.e., pulled in the direction from the right to the left in FIG. 2) by the rotation of the rotating member 8. A magnet 9 is provided in the wire 6 and a magnet 10 is provided in the wire 7.

The housing 26 includes a side portion in the longitudinal direction (in the left-right direction) of FIG. 2, and includes an endmost portion in the direction which crosses the side portion, i.e., in the width direction. The magnets 9 and 10, the wires 6 and 7, the rotating member 8, and other components denoted by the reference signs are housed in the housing and is sealed tightly from, for example, the outside.

The manipulation unit 2 includes magnets 11 and 12 in the side portion of a recessed portion of a housing 27. The magnet 11 is connected to the wire 13 and the magnet 12 is connected to the wire 14. When the bending deformation portion 1 and the manipulation unit 2 are coupled to each other, the magnet 9 and the magnet 11 stick to each other in the side portion of the housing 26, and the magnet 10 and the magnet 12 stick to each other in the side portion of the housing 26. The wires 6 and 7 of the bending deformation portion 1 may be pulled and pushed by moving the wires 13 and/or 14.

The bending deformation portion 1 further includes magnets 15 and 16, and the manipulation unit 2 further includes magnets 17 and 18.

These magnets 15, 16, 17 and 18 correspond to the coupling and decoupling unit. A part of the coupling and decoupling unit (i.e., the magnets 15 and 16) is provided in the bending deformation portion and another part (i.e., the magnets 17, 18) is provided in the manipulation unit.

The state in which the bending deformation portion 1 and the manipulation unit 2 are coupled to each other is a state in which the magnets 15 and 17 stick to each other and the magnets 16 and 18 stick to each other with the bending deformation portion 1 having been inserted in from an opening of the recessed portion of the housing 27 of the manipulation unit 2. The magnets 17 and 18 are disposed at the bottom of the recessed portion of the housing 27. The magnets 15 and 16 are connected to the rotating member 8 by a connecting member 25. Since the bending deformation portion 1 and the manipulation unit 2 are not connected (i.e., the bending deformation portion 1 and the manipulation unit 2 are not in the decoupled state) in FIG. 2, the magnets 15 and 16 are not in contact with the endmost portion of the base 5 of the bending deformation portion 1.

The rotating member 8 is in contact with the stoppers 23 and 24 by a contact portion which is included in the connecting member 25. In the decoupled state, the positions of the stoppers 23 and 24 are fixed in the bending deformation portion 1 so that the rotating member 8 pulls the wires 6 and 7, that is, so that tension is applied to the wires 6 and 7. That is, the stoppers 23 and 24 restricts the movement of the rotating member 8 toward the tip 3.

The positions of the stoppers 23 and 24 are positions at which the movement of the rotating member 8 toward the tip 3 is restricted, and are positions at which tension is applied to the wires 6 and 7 by the rotating member 8. Therefore, even when the bending deformation portion 1 and the manipulation unit 2 are in the decoupled state, tension T1 (T1>0) which is not 0 is applied to the wires 6 and 7.

The rotating member 8 is connected to one end of a spring 19. The other end of the spring 19 is connected to a fixed portion 20. The position of the other end is fixed in the bending deformation portion 1. The spring, the stoppers, and the rotating member are disposed in this order toward the base from the tip. When the state of the bending deformation portion 1 and the manipulation unit 2 is changed from the coupled state to the decoupled state, the spring 19 pulls, toward the tip 3, the rotating member 8 which has been removed from the stoppers 23 and 24 and has been in contact with the endmost portion of the base 5 so as to abut the stoppers 23 and 24.

The fixed portion 20 includes tension sensor 21 and 22. The tension sensor 21 senses the tension in the wire 6 and the tension sensor 22 senses the tension in the wire 7. When the bending deformation portion 1 and the manipulation unit 2 are in the decoupled state, the tension sensors 21 and 22 sense the tension T1.

Figure 3:
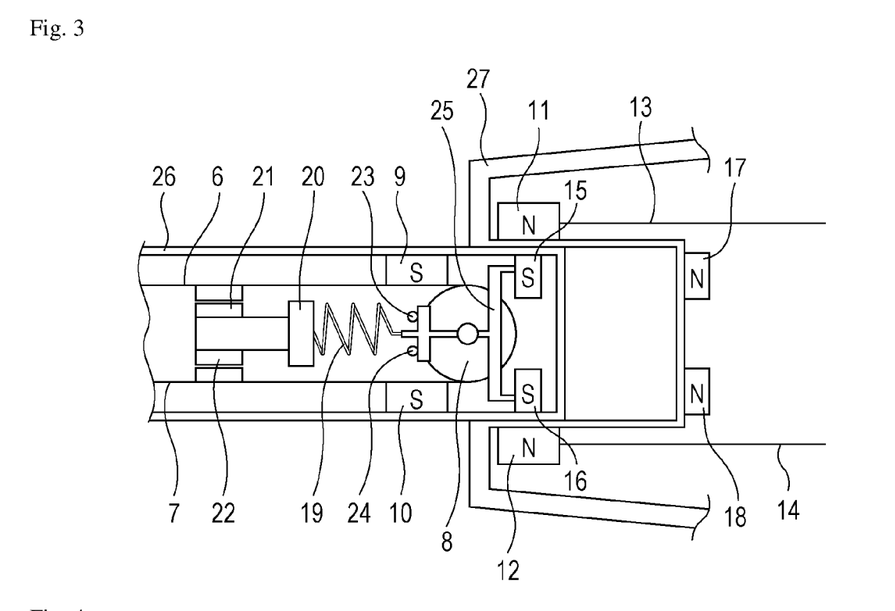
FIG. 3 is a schematic sectional view illustrating a state in which the medical instrument according to the first embodiment has been inserted but not coupled.

FIG. 3 is a schematic sectional view illustrating the medical instrument according to the present embodiment in a state in which the bending deformation portion 1 has been inserted in the recessed portion of the manipulation unit 2 but not coupled to the manipulation unit 2 (i.e., an uncoupled state).

In the state in which the bending deformation portion 1 has been inserted in the recessed portion of the manipulation unit 2 but not coupled to the manipulation unit 2, the magnets 15 and 17 do not stick to each other and the magnets 16 and 18 do not stick to each other, the rotating member is pulled by the spring 19, and the stoppers and the connecting member 25 are in contact with one another. Even in this state, the magnets 15 and 16 are not in contact with the endmost portion of the base 5.

Figure 4:
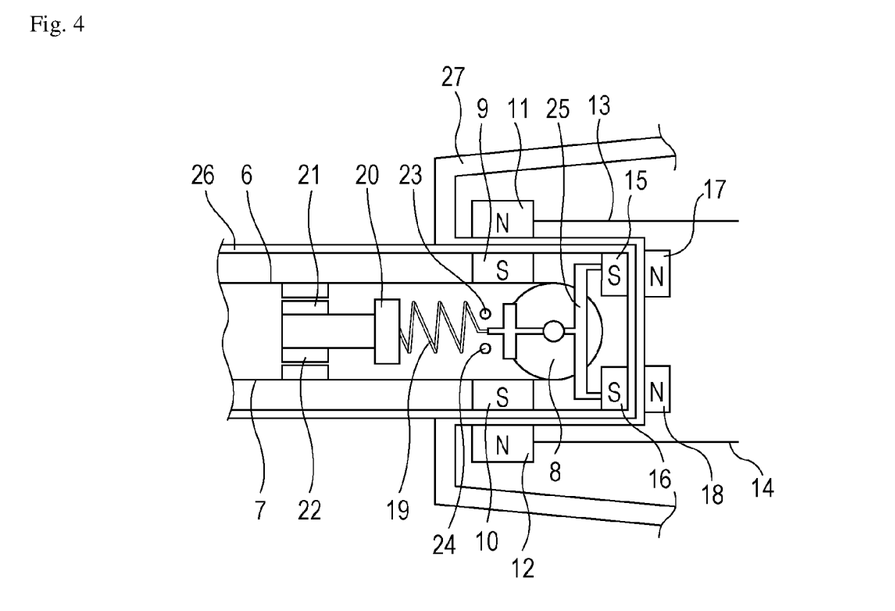
FIG. 4 is a schematic sectional view illustrating a state in which the medical instrument according to the first embodiment has been coupled.

FIG. 4 is a schematic sectional view illustrating the medical instrument according to the present embodiment in a state in which the bending deformation portion 1 has been inserted in and coupled to the recessed portion of the manipulation unit 2. The magnets 15 and 16 are coupled to the magnets 17 and 18 disposed on a bottom surface of the recessed portion of the manipulation unit 2. The rotating member 8 is moved to the right of FIG. 4 when the magnets 15 and 17 and the magnets 16 and 18 stick to one another. Then, the rotating member 8 which is the support member is moved away from the stoppers 23 and 24, and the magnets 15 and 16 are moved toward the base (in the direction from the left to the right of FIG. 4), and are brought into contact with the endmost portion of the base 5. Therefore, tension T2 which is greater than tension T1 (T1<T2) is applied to the wires 6 and 7 in a state in which no driving force is transmitted from the manipulation unit 2 (driving force: 0). With the application of tension T2, since the wires 6 and 7 are not unnecessarily slacked, power is properly transmitted to the wires and the bending deformation portion is deformed suitably (precisely).

As described above, in the medical instrument according to the present embodiment, two levels of tension (T1, T2) may be applied to the wires 6 and 7. A tension applying unit which may apply tension at two levels corresponds to the rotating member 8 and the stoppers 23 and 24. When the bending deformation portion 1 and the manipulation unit 2 are not coupled to each other, since tension in the wires of the bending deformation portion 1 is not 0, cutting, twisting, and removal from a guide of the wires due to slack may be prevented. When the bending deformation portion 1 and the manipulation unit 2 are coupled to each other, driving force from the manipulation unit 2 is transmitted suitably. If excessively large force is applied from the outside in the state in which the bending deformation portion 1 and the manipulation unit 2 are coupled to each other, since the bending deformation portion 1 and the manipulation unit 2 are decoupled from each other by a decoupling unit, tension applied to the wires becomes T1 which is smaller than T2. Therefore, cutting of the wires may be prevented. Further, if the bending deformation portion and the manipulation unit are decoupled from each other in the state in which the bending deformation portion is inserted in an object, tension equal to or greater than T2 is not applied to the wires and tension is decreased to T1. In addition, since the bending deformation portion returns to a straight form, it is easy to take the bending deformation portion out of the object.

Figure 5:
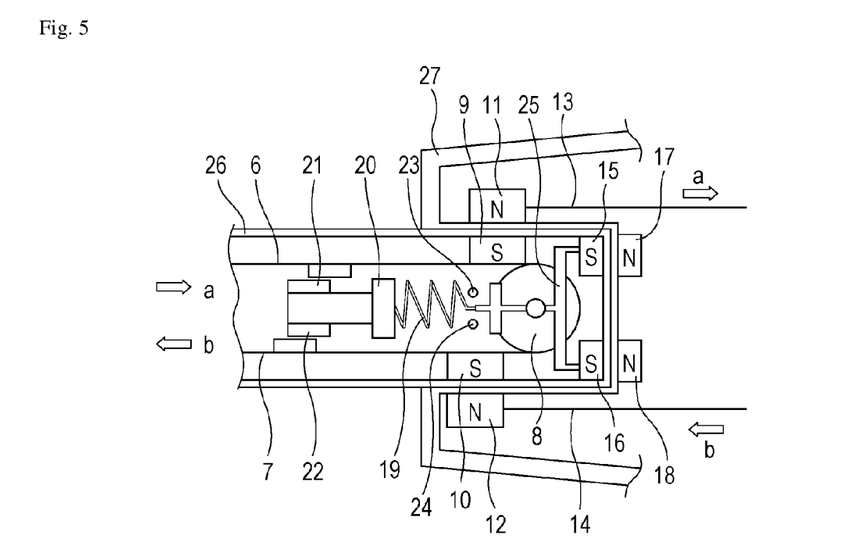
FIG. 5 is a schematic sectional view illustrating a state in which driving force is being transmitted to a wire of the medical instrument according to the first embodiment.

FIG. 5 is a schematic sectional view of the medical instrument according to the present embodiment illustrating a state in which driving force is transmitted to the wires 6 and 7 of the bending deformation portion 1 by the wires 13 and 14 of the manipulation unit 2.

The magnets 9 and 10 attached to the wires 6 and 7 stick to the magnets 11 and 12, respectively, and the wire 6 is moved in the direction of a of FIG. 5 and the wire 7 is moved in the direction of b of FIG. 5 by pulling and pushing of the wires 13 and 14. In the present embodiment, the moved amount of the wires 6 and 7 is the same because of the existence of the rotating member 8. The movement of the wires means that tension is greater than tension T2. The sensors 21 and 22 fixed to and disposed in the fixed portion 20 measure the moved amount of the wires 6 and 7, respectively, and measure tension applied to the wires. If the measured value is excessively large, an unillustrated tension control unit determines whether the shape of the bending deformation portion 1 should be kept at that shape, should be returned to the original straight shape, or should be kept at a predetermined shape.

Figure 6:
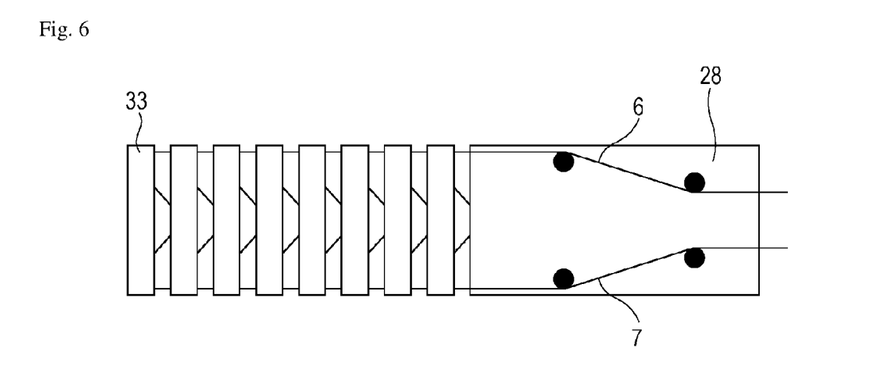
FIG. 6 is a schematic diagram illustrating a state in which the wire of the medical instrument according to the first embodiment has been disposed to an end.
Figure 7:
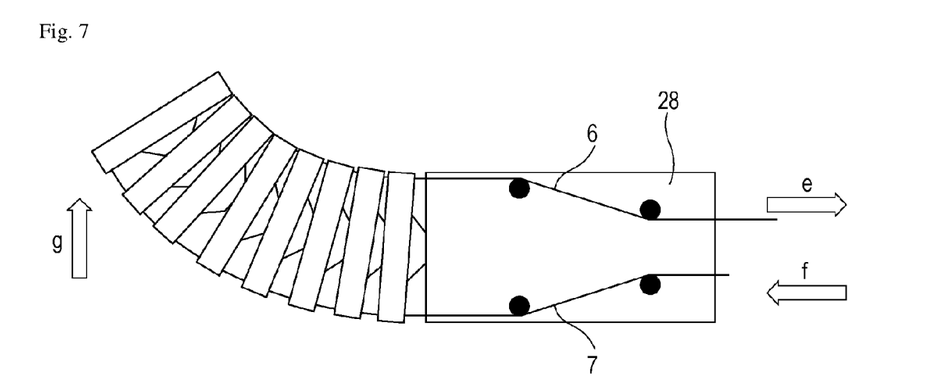
FIG. 7 is a schematic diagram illustrating a state in which the medical instrument according to the first embodiment has been deformed in a direction of g.
Figure 8:
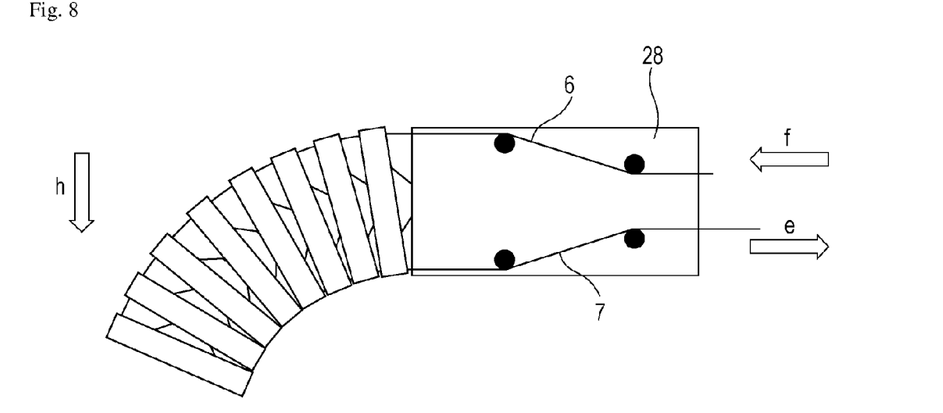
FIG. 8 is a schematic diagram illustrating a state in which the medical instrument according to the first embodiment has been deformed in a direction of h.

FIGS. 6 to 8 are schematic diagrams of the medical instrument according to the present embodiment illustrating a state in which the bending deformation portion 1 is making bending deformation by the operation of the wires.

In FIGS. 6 to 8, the reference sign 33 denotes a frame, 6 and 7 denote the wires, and 28 denotes an intermediate portion between the tip 3 and the base 5 of the bending deformation portion 1. In the present embodiment, the wires 6 and 7 are connected to the frame at the tip which is intended to make bending deformation. In FIGS. 6 to 8, four guides are illustrated as black points in the intermediate portion 28: two of them control the direction of the wire 6 and the rest of them control the direction of the wire 7. When the wires are pulled or pushed in the directions of e and/or f as illustrated in FIG. 7 or 8, the bending deformation portion makes bending deformation in the direction illustrated by g or h.

Figure 9:
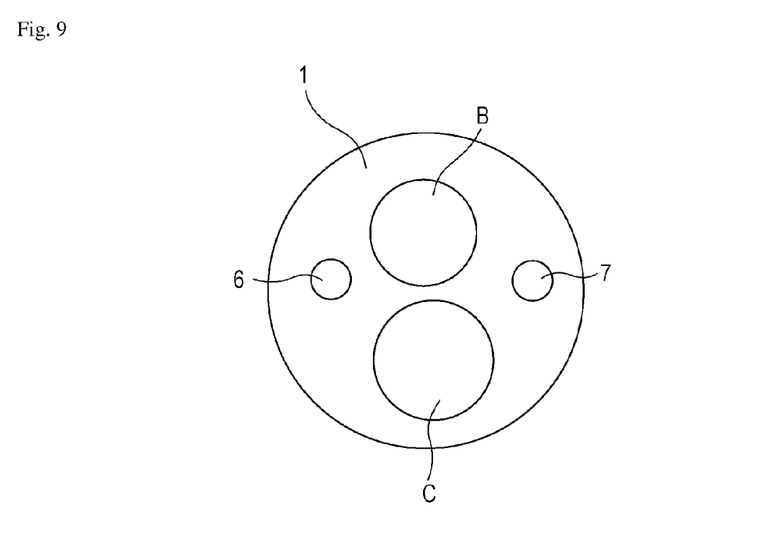
FIG. 9 is a schematic diagram illustrating a tip of the medical instrument according to the first embodiment seen from the front.

FIG. 9 is a schematic sectional view illustrating the tip of the bending deformation portion of an endoscope as the medical instrument according to the present embodiment. The bending deformation portion 1 includes the wires 6 and 7 to reach the tip thereof. The bending deformation portion 1 includes two cylindrical spaces (B, C). An image pickup optical system, such as optical fiber, of the endoscope is disposed in one of the space, and lighting equipment, a treatment tool, and the like are disposed in the other of the space.

The medical instrument according to the present invention may be used with the bending deformation portion being inserted in, for example, the large intestine, flesh which is cut open, the mouth, the head, and the ear.

In the bending deformation portion 1 of the present embodiment, the wires and the coupling and decoupling unit are disposed inside the housing so that the components are protected from blood, a cleaning liquid, and the like. However, in the medical instrument according to the present invention, either one of the wires or the coupling and decoupling unit, or a part of the coupling and decoupling unit may be disposed outside the bending deformation portion when the bending deformation portion and the manipulation unit are coupled to each other.

In the present embodiment, the rotating member is desirable since it may synchronize the movement of the two wires. Although two wires are provided in the rotating member in the medical instrument according to the present invention, a single wire wound around the rotating member may be used to cause the same operation as that of the wires 6 and 7. If the two wires are not moved synchronously, another unit, may be included without using the rotating member, or each of the wires may be manipulated by the manipulation unit without using the rotating member.

The treating instrument includes two wires in the present embodiment in order to cause bending deformation in the directions of g and h as illustrated in FIGS. 7 and 8. However, the medical instrument according to the present invention may include further wire(s) for causing bending deformation in direction(s) different from the directions of g and h, for example, the directions to cross the directions of g and h, in more specific, the directions to perpendicularly cross the directions g and h (i.e., the direction from the near side to the far side and vice versa of FIGS. 7 and 8).

Although the medical instrument according to the present embodiment is an endoscope, the medical instrument according to the present invention may also be, for example, a medical instrument which does not include an image pickup optical system but includes a treatment tool in a cylindrical accommodation space, and a medical instrument which does not include an image pickup optical system but includes a position sensor.

Second Embodiment

A medical instrument according to a second embodiment of the present invention is the same as that of the first embodiment except that a bending deformation portion 1 and a manipulation unit 2 are coupled to each other with a part of an coupling and decoupling unit included in the bending deformation portion 1 being disposed outside.

Figure 10:
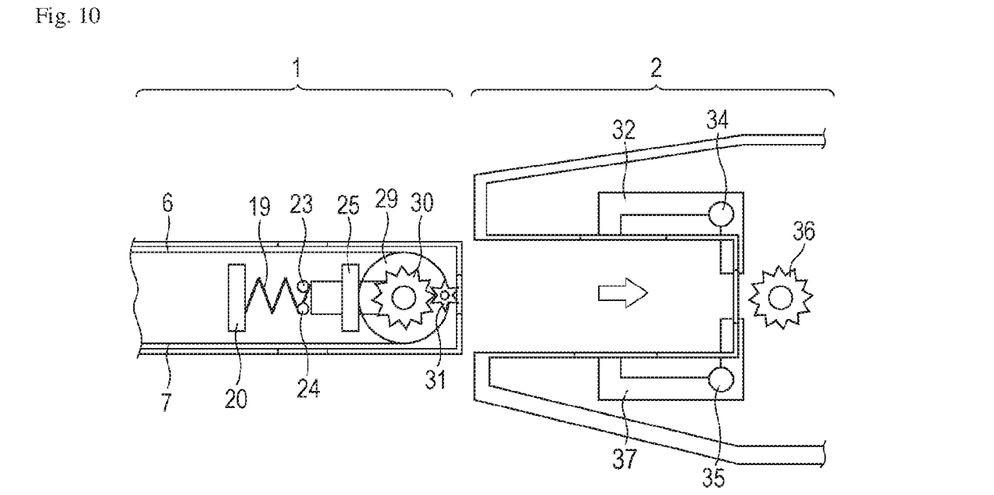
FIG. 10 is a schematic sectional view illustrating a state in which a medical instrument according to a second embodiment has been decoupled.

FIG. 10 is a schematic sectional view illustrating the medical instrument according to the present embodiment. In FIG. 10, the bending deformation portion 1 and the manipulation unit 2 are in a decoupled state. In the bending deformation portion 1, a support member 29, which rotates, supports wires 6 and 7. The support member 29 includes a gear 30 which is a first gear and a gear 31 which is a second gear. The first gear 30 and the second gear 31 mesh each other. The support member 29 is provided in a connecting member 25, and the connecting member 25 includes a flange. The connecting member 25 is connected to one end of a spring 19. The other end of the spring 19 is connected to a fixed portion 20. A movement of the connecting member in the direction from the right to the left in FIG. 10 is restricted by stoppers 23 and 24.

The manipulation unit 2 includes fulcrums 34 and 35 for rotating levers 32 and 37, respectively. The manipulation unit 2 includes an opening at the bottom of a recessed portion of a housing. A gear 36 which is a third gear is provided at the opening. In an illustrated state in which the bending deformation portion 1 and the manipulation unit 2 are decoupled from each other, the position of the support member 29 is fixed by the stoppers 23 and 24 so that tension T1 is applied to the wires 6 and 7.

Figure 11:
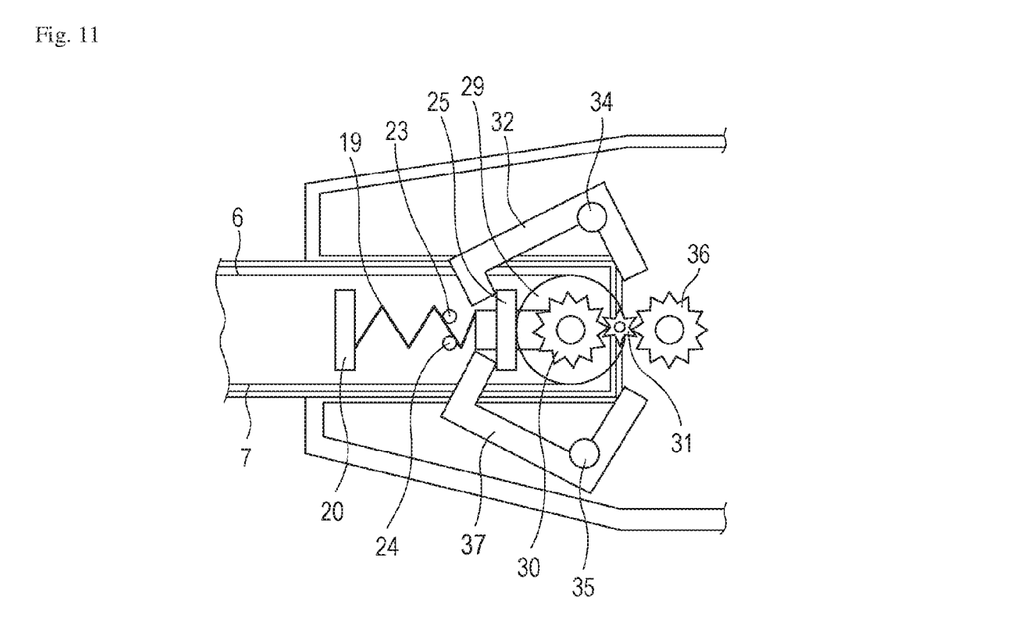
FIG. 11 is a schematic sectional view illustrating a state in which the medical instrument according to the second embodiment has been coupled.

FIG. 11 is a schematic sectional view illustrating a state in which the bending deformation portion 1 and the manipulation unit 2 are coupled to each other. When the bending deformation portion 1 is inserted in the recessed portion of the manipulation unit 2 and an end of the bending deformation portion 1 reaches an end of the recessed portion, the levers 32 and 37 rotate and claws clamp the flange of the connecting member 25. When the claws clamp the flange of the connecting member, the coupled state is established.

When the claws of the levers 32 and 37 clamp the flange of the connecting member in the coupled state, the connecting member 25 which includes the support member 29 is moved toward a base (i.e., in the direction from the left to the right in FIG. 11). When the connecting member 25 is moved, the second gear 31 included in the support member 29 is moved to a position at which the second gear 31 is disposed outside the bending deformation portion 1 and meshes with the third gear 36. Since the connecting member 25 is pulled by the spring 19, tension T2 which is greater than tension T1 is applied to the wires 6 and 7.

Figure 12:
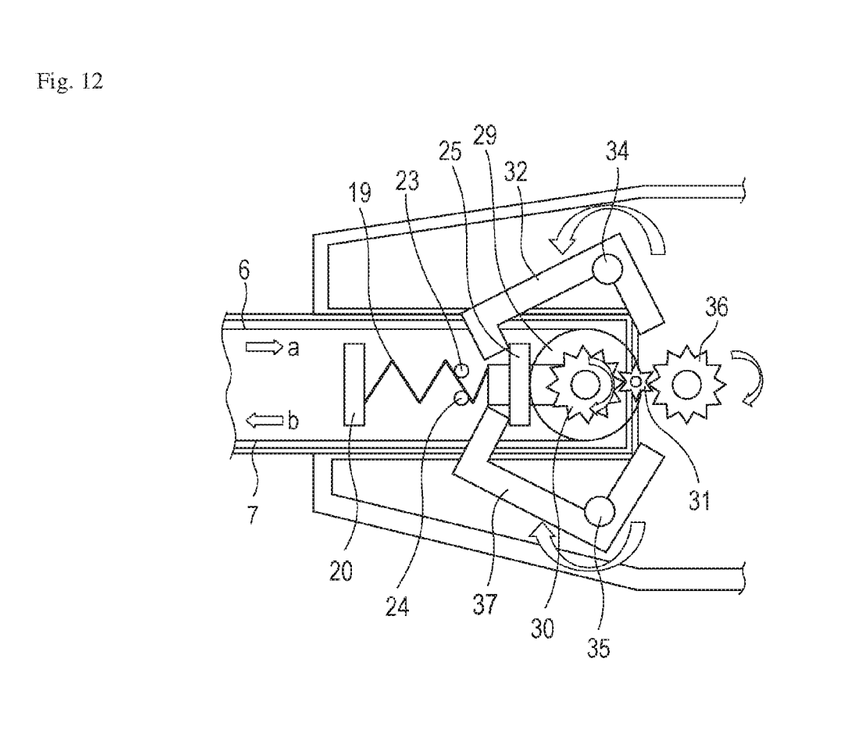
FIG. 12 is a schematic sectional view illustrating a state in which driving force is being transmitted to a wire of the medical instrument according to the second embodiment.

FIG. 12 is a schematic sectional view illustrating a state in which the wires of the medical instrument according to the present embodiment are being driven. The support member 29 is rotated when mutually meshed gears (i.e., the third gear 36 and the second gear 31, and the second gear 31 and the first gear 30) rotate, and the wires 6 and 7 are pulled and pushed in the left-right direction (the directions of a and b) of FIG. 12. Each of the embodiments has been described in detail above. In the medical instrument of the present invention, tension T1 of which size is greater than 0 and is smaller than T2 is applied to the bending deformation portion in the decoupled state. Therefore, slack of the wire is prevented and damage to the bending deformation portion (i.e., damage to the wire) may be prevented. In addition, since tension T2 which is greater than T1 is applied to the bending deformation portion in the coupled state, power is properly transmitted to the wires during the operation, whereby the bending deformation portion is deformed suitably.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-124502, filed May 31, 2012, which is hereby incorporated by reference herein in its entirety.

INDUSTRIAL APPLICABILITY

The present invention can be applied to medical instruments, especially to an endoscope or a medical treatment tool which are inserted in a living body for a treatment.

The invention claimed is:

1. A medical instrument having
   an elongated bending deformation portion which includes a wire therein and which is bent by driving the wire; and
   a manipulation unit which transmits power to the wire and which is detachable from the bending deformation portion,
   wherein,
      the bending deformation portion has a tension applying unit which applies tension to the wire; and
      a relationship between tension T1 in the wire applied by the tension applying unit when the bending deformation portion and the manipulation unit are decoupled and tension T2 in the wire applied by the tension applying unit when the bending deformation portion and the manipulation unit are coupled satisfies $0<T1<T2$,
   wherein the tension applying unit and the wire are included in the bending deformation portion so as not to be exposed to an external at a state where the bending deformation portion and the manipulation unit are decoupled,
   wherein the tension applying unit includes:
      a stopper which restricts a position of a support member which supports the wire in order to apply tension T1 to the wire when the bending deformation portion and the manipulation unit are decoupled from each other; and
      the support member which may be moved further toward a base than the position in order to apply tension T2 to the wire when the bending deformation portion and the manipulation unit are coupled to each other.

2. The medical instrument according to claim 1, wherein the support member is a rotating member which is rotated, and wherein a spring, the stopper, and the rotating member are disposed in this order from the tip toward the base.

3. The medical instrument according to claim 2, wherein the bending deformation member includes another wire, and further wherein the wire and the another wire is moved in mutually different directions in accordance with a rotation of the rotating member.

4. The medical instrument according to claim 1, wherein the bending deformation portion includes a plurality of frames at a tip thereof and makes bending deformation among the plurality of frames.

5. The medical instrument according to claim 1, wherein the bending deformation portion includes a magnet and the manipulation unit also includes a magnet.

6. The medical instrument according to claim 5, wherein the magnet included in the bending deformation portion and the magnet included in the manipulation unit stick to each other when the bending deformation portion is inserted in the manipulation unit.

7. The medical instrument according to claim 6, wherein the bending deformation portion further includes a support member which supports the wire in order to apply tension thereto, and further wherein the support member is moved when the magnet included in the bending deformation portion and the magnet included in the manipulation unit stick to each other.

8. The medical instrument according to claim 1, wherein the manipulation unit has an indentation to which the bending deformation portion is coupled.

9. The medical instrument according to claim 1, wherein the bending deformation portion further comprises a tension sensing unit that senses the tension of the wire.

10. A bending deformation device of a medical instrument having a wire therein and which is bent by driving the wire by a manipulation device,
wherein,
the bending deformation device further has a tension applying unit which applies tension to the wire; and
a relationship between tension T1 in the wire applied by the tension applying unit when the bending deformation device and the manipulation device are decoupled and tension T2 in the wire applied by the tension applying unit when the bending deformation device and the manipulation device are coupled satisfies 0<T1<T2, and
wherein the tension applying unit and the wire are included in the bending deformation device so as not to be exposed to an external at a state where the bending deformation device is decoupled from the manipulation unit,
wherein the tension applying unit includes:
a stopper which restricts a position of a support member which supports the wire in order to apply tension T1 to the wire when the bending deformation device and the manipulation device are decoupled from each other; and
the support member which may be moved further toward a base than the position in order to apply tension T2 to the wire when the bending deformation device and the manipulation device are coupled to each other.

11. The bending deformation device according to claim 10, wherein the support member is a rotating member which is rotated, and wherein a spring, the stopper, and the rotating member are disposed in this order from the tip toward the base.

12. The bending deformation device according to claim 11, further including another wire, and further wherein the wire and the another wire is moved in mutually different directions in accordance with a rotation of the rotating member.

13. The bending deformation device according to claim 10, wherein the bending deformation device includes a plurality of frames at a tip thereof and makes bending deformation among the plurality of frames.

14. The bending deformation device according to claim 10, wherein the bending deformation device includes a magnet and the manipulation device also includes a magnet.

15. The bending deformation device according to claim 14, wherein the magnet included in the bending deformation device and the magnet included in the manipulation device stick to each other when the bending deformation device is inserted in the manipulation device.

16. The bending deformation device according to claim 15, wherein the bending deformation portion further includes a support member which supports the wire in order to apply tension thereto, and further wherein the support member is moved when the magnet included in the bending deformation device and the magnet included in the manipulation device stick to each other.

17. The bending deformation device according to claim 10, further comprises a tension sensing unit that senses the tension of the wire.

* * * * *